(12) United States Patent
Zhang et al.

(10) Patent No.: US 9,746,579 B2
(45) Date of Patent: Aug. 29, 2017

(54) CT SYSTEMS AND METHODS THEREOF

(71) Applicants: Tsinghua University, Beijing (CN); Nuctech Company Limited, Beijing (CN)

(72) Inventors: Li Zhang, Beijing (CN); Zhiqiang Chen, Beijing (CN); Qingping Huang, Beijing (CN); Xin Jin, Beijing (CN); Yunda Sun, Beijing (CN); Le Shen, Beijing (CN); Ji Zhao, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 228 days.

(21) Appl. No.: 14/576,737

(22) Filed: Dec. 19, 2014

(65) Prior Publication Data
US 2015/0185355 A1    Jul. 2, 2015

(30) Foreign Application Priority Data

Dec. 26, 2013    (CN) .......................... 2013 1 0739803

(51) Int. Cl.
*A61B 6/00* (2006.01)
*G01V 5/00* (2006.01)
(Continued)

(52) U.S. Cl.
CPC ........... *G01V 5/005* (2013.01); *G01N 23/046* (2013.01); *G01T 7/08* (2013.01); *G06T 11/003* (2013.01);
(Continued)

(58) Field of Classification Search
CPC ........ G01N 23/046; G01T 7/08; G01V 5/005; G06T 11/003; G06T 2207/10072;
(Continued)

(56) References Cited

U.S. PATENT DOCUMENTS 7,233,644 B1 *  6/2007  Bendahan ............ G01N 23/046
                                                   378/57
7,324,625 B2 *  1/2008  Eilbert .................... A61B 6/482
                                                   378/57
(Continued)

FOREIGN PATENT DOCUMENTS

JP    2000-235007 A    8/2000
WO    2004090576 A2   10/2004

OTHER PUBLICATIONS

European search report, dated May 11, 2015, in corresponding European application No. 14199265.1.
(Continued)

*Primary Examiner* — Irakli Kiknadze
(74) *Attorney, Agent, or Firm* — Browdy and Neimark, PLLC (57) ABSTRACT

A CT system and method thereof are disclosed. The system includes: a conveyor mechanism; a first scanning stage configured to scan the object and generate a first digital signal; a second scanning stage spaced from the first scanning stage at a preset distance in a direction of the object's movement; a processing device configured to reconstruct a CT image of the object at a first image quality based on the first digital signal, and analyze the CT image; and a control device configured to adjust a scanning parameter of the second scanning stage based on an analysis result of the processing device to cause the second scanning stage to output a second digital signal. The processing device reconstructs a CT image of the object at a second image quality higher than the first image quality at least based on the second digital signal. The system takes full advantage of the distributed ray sources which replace the normal slip ring technology.

14 Claims, 3 Drawing Sheets

(51) Int. Cl.
*G01N 23/04* (2006.01)
*G01T 7/08* (2006.01)
*G06T 11/00* (2006.01)

(52) U.S. Cl.
CPC . *G06T 2207/10072* (2013.01); *G06T 2211/40* (2013.01)

(58) Field of Classification Search
CPC ....... G06T 2211/40; A61B 6/032; A61B 6/04; A61B 6/4266; A61B 6/502; A61B 6/548; A61B 8/0825; A61B 8/4209; A61B 8/4218; A61B 8/483; A61B 8/565; A61B 8/58; A61B 6/025; A61B 6/06; A61B 6/4291; A61B 6/583; A61B 6/4233; A61B 5/0456; A61B 6/027; A61B 6/4085; A61B 6/4441; A61B 6/482; A61B 6/466; A61B 6/488; A61B 6/504; A61B 6/037; A61B 6/4014; A61B 6/542; A61B 6/541; A61B 6/4028; A61B 6/4007; A61B 6/4488; A61B 6/035; A61B 6/5205; A61B 6/4035; A61B 6/4241; A61B 6/508
USPC .......................................... 378/4, 19, 20, 57
See application file for complete search history.

(56) References Cited

U.S. PATENT DOCUMENTS

| 2008/0037707 A1* | 2/2008 | Rothschild | G01N 23/046 378/57 |
| 2008/0056436 A1* | 3/2008 | Pack | G01N 23/046 378/10 |
| 2011/0091013 A1* | 4/2011 | Muenster | G01V 5/0058 378/57 |
| 2011/0176659 A1* | 7/2011 | Rogers | A61B 6/032 378/57 |

OTHER PUBLICATIONS

First Examination Report issued in corresponding Australian Patent Application No. 2014373004, dated Nov. 18, 2016.
Japanese Office Action for JP2016-543121 dated Jun. 5, 2017 and English language translation.
Canadian First Examination Report dated Apr. 20, 2017 for corresponding Canadian Application No. 2,935,086.
Singapore First Examination Report dated Jun. 29, 2017 for corresponding Singapore Application No. 11201605156W.

* cited by examiner

CT SYSTEMS AND METHODS THEREOF

CROSS-REFERENCE TO RELATED APPLICATIONS

This application claims priority to the Chinese Patent Application No. 201310739803.4 filed on Dec. 26, 2013, the entire content of which is incorporated herein by reference in its entirety.

TECHNICAL FIELD

Embodiments of the present disclosure relate to radiography and security inspection technology, and more particularly, to multi-source static Computed Tomography (CT) system and method for security inspection of luggage and articles.

BACKGROUND

CT technology has been playing an important role in occasions such as security inspection, thanks to its capability of eliminating influence from object overlapping. Conventional CT apparatuses use a slip ring device, and acquire projection data at different angles by rotating X-ray source and detectors. Then, the CT apparatuses reconstruct a tomogram image to obtain information of the inside of the inspected luggage or articles. In combination with dual-energy or multi-energy imaging technology, the existing inspection apparatuses can reconstruct atomic number and electron density of the inspected object, and identify materials contained in article, achieving good effects in detecting explosives or drugs, for example.

The existing CT technology for security inspection has disadvantages. First, there is a problem with the scanning speed. A high speed is helpful to mitigation of pressure caused by a large number of passengers and cargoes. However, a high-speed scanning typically requires a slip ring that can rotate at a high speed. Due to difficulties in fabrication precision and reliability, for example, the high-speed slip ring is very expensive in manufacture and maintenance, and thus is difficult in popularization. Second, there exist problems such as false alarm and missing alarm. It is difficult for the automatic identification and alarm functions in the CT technology to achieve an accuracy of 100%, and thus detection of contraband still requires manual auxiliary examination, and sometimes it even requires opening a luggage case for examination. Such examination often takes several or tens of minutes, which increases labor and time cost and limits improvement in examination efficiency. In order to address these problems, an apparatus using secondary scanning technology has been introduced into market, which can reduce a frequency of opening the luggage case by performing a high-accuracy secondary scanning on any suspicious luggage case to improve CT image quality. This secondary scanning, however, also results in increased scanning time and interruption in the security inspection process.

In recent years, the technology of carbon-nanotube X-ray tube has been introduced to practical applications. Unlike normal X-ray sources, the carbon-nanotube X-ray tube does not require high temperature for generating rays. Instead, it generates cathode rays based on principle of discharging of carbon-nanotube tip, and uses the cathode rays to strike a target to generate X rays. Such X-ray source has advantages of rapid switch-on/off, and a smaller volume. A "static CT" apparatus without rotation can be formed by arranging the X-ray source properly and irradiating X-rays onto the object from different directions. This significantly accelerates the radiography process while omitting the slip-ring structure and saving cost, thereby contributing a lot to the field of security inspection.

SUMMARY

In view of one or more problems with the conventional technology, embodiments of the present disclosure provide a CT system and method.

According to an aspect of the disclosure, a CT system is provided comprising: a conveyor mechanism configured to convey and move an object under inspection linearly; a first scanning stage comprising a first ray source, a first detector, and a first data acquisition device, and configured to scan the object and generate a first digital signal; a second scanning stage configured to be spaced from the first scanning stage at a preset distance in a direction of the object's movement, and comprising a second ray source, a second detector, and a second data acquisition device; a processing device configured to reconstruct a CT image of the object at a first image quality based on the first digital signal, and analyze the CT image; and a control device configured to adjust a scanning parameter of the second scanning stage based on an analysis result of the processing device to cause the second scanning stage to output a second digital signal, wherein the processing device reconstruct a CT image of the object at a second image quality higher than the first image quality at least based on the second digital signal.

In an embodiment, when the second scanning stage scans a part of the object, the control device adjusts the scanning parameter of the second scanning stage based on an analysis result of the processing device corresponding to the part, to cause the second scanning stage to output the second digital signal.

In an embodiment, the CT system further comprises a third scanning stage that comprises a third ray source, a third detector, and a third data acquisition device, the control device is configured to adjust a scanning parameter of the third scanning stage based on the CT image of at least the first image quality to cause the third scanning stage to output a third digital signal, and the processing device is configured to reconstruct a CT image of the object at a third image quality higher than the first image quality at least based on the third digital signal.

In an embodiment, when the third scanning stage scans a part of the object, the control device adjusts the scanning parameter of the third scanning stage based on an analysis result of the processing device corresponding to the part, to cause the third scanning stage to output the third digital signal.

In an embodiment, each of the first, second and third scanning stages uses a sparse-view scanning mode.

In an embodiment, each of the first, second and third scanning stages uses a limited-angle scanning mode.

In an embodiment, each of the first, second and third ray source comprises a plurality of source points provided in a plurality of scanning planes perpendicular or nearly perpendicular to the direction of the object's movement, and in each of the scanning planes the source points are distributed along one or more continuous or discontinuous segments of line or arc.

In an embodiment, the source points of the second scanning stage are preset to use an increased voltage to increase ray energy when the analysis result of the processing device indicates that an increased penetrability is required to discern a metal object and its neighborhood.

In an embodiment, the source points of the second scanning stage are preset to use an increased number of ray sources to increase a spatial resolution when the analysis result of the processing device indicates that it is required to discern tiny objects.

In an embodiment, the source points of the second scanning stage are adjusted to have a preset number of activated ray sources when the analysis result of the processing device indicates that it is required to complete scanning within a prescribed time period.

In an embodiment, a beam spectrum for the source points of the second scanning stage is adjusted when the analysis result of the processing device indicates that a more accurate material identification is required.

In an embodiment, a beam intensity of the source points of each of the first, second and third scanning stages can be adjusted according to a number of ray sources preset in the plane where the source points are provided.

In an embodiment, when the number of the source points is large, the beam intensity is increased to reduce beam-emitting time of each source point and thus ensure completion of scanning within a prescribed time period; when the number of the source points is small, a high beam intensity is used to increase a signal-to-noise ratio of scan data.

According to another aspect of the disclosure, a method for a CT system is provided, the CT system comprising a first scanning stage, and a second scanning stage spaced from the first scanning stage at a preset distance in a moving direction of an object under inspection, the method comprises: scanning the object by the first scanning stage during the movement of the object, and generating a first digital signal; reconstructing a CT image of the object at a first image quality based on the first digital signal, and analyzing the CT image; and adjusting a scanning parameter of the second scanning stage based on an analysis result to cause the second scanning stage to output a second digital signal; and reconstructing a CT image of the object at a second image quality higher than the first image quality at least based on the second digital signal.

According to the embodiments of the present disclosure, scanning based on multi-plane and adaptive scanning parameter is performed in a single scanning process. This achieves high-accuracy scanning and speeds up the scanning processing while obtaining better image quality and increased identification accuracy.

BRIEF DESCRIPTION OF THE DRAWINGS

For a better understanding of the present disclosure, embodiments of the present disclosure will be described below with reference to figures in which.

DETAILED DESCRIPTION OF THE EMBODIMENTS

The particular embodiments of the disclosure are described below in details. It shall be noted that the embodiments herein are used for illustration only, but not limiting the disclosure. In the description below, a number of particular details are explained to provide a better understanding to the disclosure. However, it is apparent to those skilled in the art the disclosure can be implemented without these particular details. In other examples, well-known circuits, materials or methods are not described so as not to obscure the disclosure.

Throughout the specification, reference to "one embodiment," "an embodiment," "one example" or "an example" means that the specific features, structures or properties described in conjunction with the embodiment or example are included in at least one embodiment of the present disclosure. Therefore, the phrases in "one embodiment," in "an embodiment," in "one example" or in "an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that figures here are for the purpose of illustration, and not necessarily drawn to scale. It should be appreciated that "connecting" or "coupling" a component to another component may mean that the component is directly connected or coupled to the other component, or there may be a component intervening between them. On the contrary, "directly connecting" or "directly coupling" a component to another component mans that there is no intervening component. Like reference signs refer to similar elements throughout the figures. The term "and/or" used herein means any and all combinations of one or more listed items.

In view of the problem with the conventional technology, embodiments of the present disclosure propose a static CT system having multiple X-ray sources. When a conveyor mechanism conveys and moves linearly an object under inspection, a first scanning stage scans the object and generates a first digital signal. Then, a CT image of a first image quality is reconstructed for the object based on the first digital signal, and the CT image is analyzed. Next, a scanning parameter of a second scanning stage is adjusted based on the analysis result, so that the second scanning stage outputs a second digital signal. The second scanning stage is provided apart from the first scanning stage at a preset distance in the direction of the object's movement. A CT image of a second image quality is then reconstructed for the object at least based on the second digital signal. The second image quality is higher than the first image quality. By using distributed X-ray sources, it is possible to avoid use of a high-speed slip ring, and increase the inspection speed while reducing cost for device manufacture and maintenance. The scanning method based on multi-plane and adaptive scanning parameter can integrate the two high-accuracy scanning processes in the slip-ring solution into a single scanning flow, and achieve higher image quality and increased identification accuracy while saving time and labor. The present disclosure can contribute to acceleration of the CT scanning process in security inspection and improvement of accuracy in identifying contraband, and can be widely used in public places like station, airport and customs.

Figure 1:
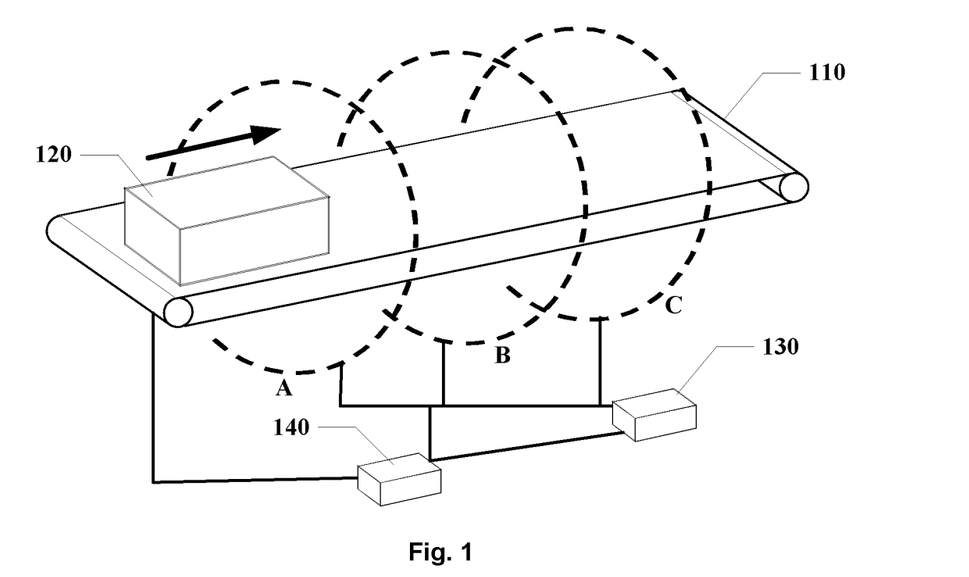
FIG. 1 illustrates a schematic block diagram of a CT system according to an embodiment of the disclosure.

FIG. 1 illustrates a schematic block diagram of a CT system according to an embodiment of the disclosure. As shown in FIG. 1, the multi-source static CT system for security inspection of luggage and articles may include multiple scanning stages (i.e., the first scanning stage A, the second scanning stage B, the third scanning stage C, . . . ), a conveyor mechanism 110, a control device 140, and a processing device 130. The respective scanning stages are provided apart from each other at a preset distance in the direction of the object's movement. Each scanning stages includes a ray source, a detector and an acquisition device. Here, the ray sources may include a plurality of distributed X-ray source points.

In the shown embodiments, the conveyor mechanism 110 conveys and moves the object 120 under inspection linearly. The first scanning stage A includes a first ray source, a first detector, and a first data acquisition device, and is configured to scan the object and generate a first digital signal. The second scanning stage B is configured to be spaced from the first scanning stage at a preset distance in a direction of the object's movement, and includes a second ray source, a second detector, and a second data acquisition device. The processing device 130 is configured to reconstruct a CT image of the object at a first image quality based on the first digital signal, and analyze the CT image. The control device 140 is couple with the respective scanning stages and the processing device 130. The control device 140 adjusts a scanning parameter of the second scanning stage based on an analysis result of the processing device 130 to cause the second scanning stage to output a second digital signal. The processing device 130 reconstructs a CT image of the object at a second image quality higher than the first image quality at least based on the second digital signal (that is, based on the second digital signal, or based on the first and second digital signals).

According to some embodiments, when the second scanning stage scans a part of the object, the control device adjusts the scanning parameter of the second scanning stage based on an analysis result of the processing device corresponding to the part, to cause the second scanning stage to output the second digital signal. In an example where 100 slices (tomograms) need to be reconstructed for a target luggage case, after the first scanning stage scans the 8th slice, the processing device (e.g., computer) reconstructs and analyzes this slice, and estimates a scanning parameter for the second and subsequent scanning stages to scan this slice. When the part of the object corresponding to the $8^{th}$ slice passes through the second scanning stage, the second scanning stage adjusts the parameter based on the analysis result, and scans the object. This is, the scanning parameter is adjusted differently when different parts of the object pass through the second scanning stage.

The third scanning stage C includes a third ray source, a third detector, and a third data acquisition device. The control device 140 adjust a scanning parameter of the third scanning stage C based on the CT image of the first image quality (e.g., the first resolution) to cause the third scanning stage to output a third digital signal, and the processing device reconstructs a CT image of the object at a third image quality higher than the first image quality at least based on the third digital signal (that is, based on the third digital signal, or based on the third digital signal and at least one of the first and second digital signals). When the third scanning stage scans a part of the object, the control device adjusts the scanning parameter of the third scanning stage based on an analysis result of the processing device corresponding to the part, to cause the third scanning stage to output the third digital signal.

Each of the multi-point distributed X-ray source module may have, for example, one or more source points. The energy for each source point may be set, and the order in which the source points are activated may be set. In the system, the source points are distributed on multiple scanning planes (which are perpendicular or nearly perpendicular to the channel travel direction). In each plane, the source points are distributed in one or more continuous or discontinuous segments of line or arc. Since the energy for each source point may be set, several scanning modes may be implemented during the beam-emitting process in which different source points may have different energy spectra, or energy for source points in different planes may be different. The source points may be divided into different groups. For example, the source points in each module or in each plane may be classified into a group. The order in which the source points in the same group cause electrons to strike a target is adjustable, and it is possible to implement sequential or alternate beam emission. Source points in different groups may be activated simultaneously to scan, and thus the scanning speed is increased.

Each of the scanning stages includes a complete set of area array X-ray detector, sense circuit, acquisition-trigger signal circuit, and data transfer circuit. The ray sources are distributed in multiple planes, and thus a corresponding detector array is provided for each plane. The detector array is arranged in a circle or an arc. The central column of detectors may be in the same plane where the ray sources are located (when the source points are provided at a part of the circle, the detectors may be placed at the remaining part of the circle), or in a plane parallel to the plane where the ray sources are located (when the source points are distributed along the circle, there is no remaining room for placing the detectors). The distance between the two planes where the ray sources and the detectors are located respectively should be kept as small as possible to alleviate the Oblique Effect due to the fact that the ray sources and the source points are not in the same plane. The detector array may have one or more rows, and the detectors may be of single-energy, dual-energy or spectral type.

The conveyor mechanism 110 includes a carrier table or a conveyance tape. The control device 140 controls the X-ray machine and a rack for the detectors. By controlling the beam-emitting mode of the distributed ray sources or the translation movement of the object or combination thereof, it is possible to implement scanning in a spiral, circular or other special trajectory.

The control device 140 is responsible for control over operations of the CT system including mechanic rotation, electrical control, and safety interlock control. The control device 140 particularly controls beam energy and sequence of the ray sources, and readout of detector data and data reconstruction.

Figure 2:
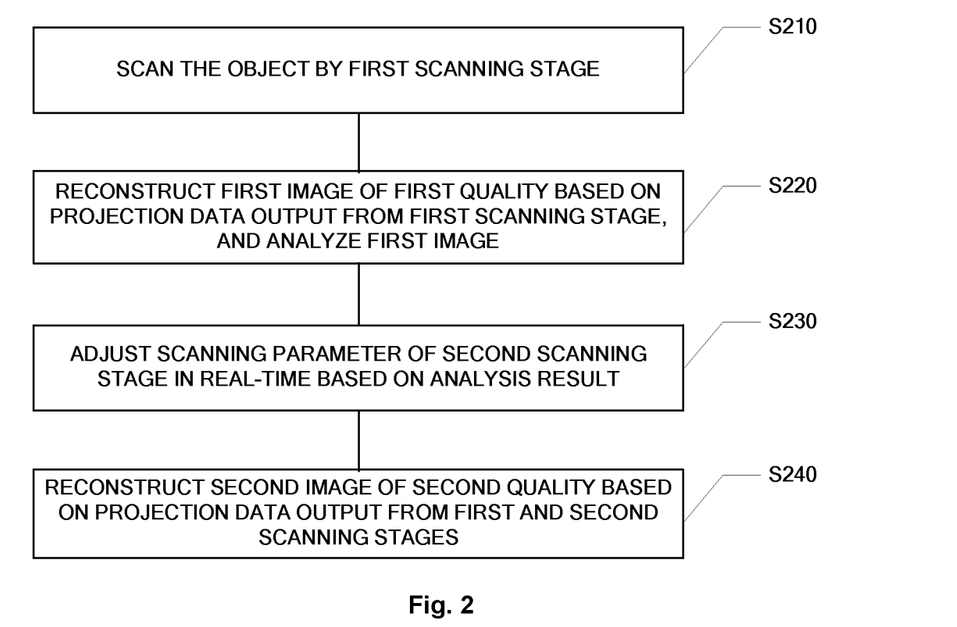
FIG. 2 illustrates a flowchart of a method for a CT system according to an embodiment of the disclosure.

FIG. 2 illustrates a flowchart of a method for a CT system according to an embodiment of the disclosure. As shown in FIG. 2, the object is scanned by the first scanning stage during the movement of the object, and a first digital signal is generated at step S210. When the object 120 (e.g., luggage case) is imported to the system by the conveyor mechanism 110, the ray sources and detectors in the first plane A of the system scan the luggage case, and transfer the scan data to the processing device 130 for CT reconstruction. At the same time, the system records the time and location at which the scanned part of the luggage case passes through the first plane. It is possible to calculate when the scanned part will pass through the subsequent plane based on the tape speed and coding.

At step S220, a CT image of the object at a first image quality is reconstructed based on the first digital signal, and the CT image is analyzed.

In an example, the processing device 130 determines the overall feature of the scanned part of the luggage case according to the CT reconstruction result. The determination may be made as to whether there are many high-density materials (e.g., metals), whether there are many minutious substances (tiny articles), and whether there is any suspicious object in the luggage case.

At step S230, a scanning parameter of the second scanning stage is adjusted based on an analysis result of the processing device to cause the second scanning stage to output a second digital signal.

The control device 140 sets in advance the scanning parameter (e.g., ray source voltage, current, the number of ray sources to be activated) for the subsequent scanning stage based on the analysis result. For example, the source points of the subsequent scanning stage may be preset to use an increased voltage to increase ray energy when an increased penetrability is required to discern a metal object and its neighborhood. The source points of the subsequent scanning stage may be preset to use an increased number of ray sources to increase, for example, a spatial resolution when it is required to discern tiny objects. A beam intensity of each source point may also be adjusted according to the number of activated ray sources preset in the plane where the source point is provided, so that the scanning process can be completed with a prescribed time period. For example, when the number of the source points is large, the beam intensity is increased to reduce beam-emitting time of each source point; when the number of the source points is small, a high beam intensity is used to increase a signal-to-noise ratio of scan data and improve noise level in the reconstructed image.

At step S240, a CT image of the object is reconstructed at a second image quality higher than the first image quality at least based on the second digital signal.

For example, when a part of the object 120 passes through the subsequent scanning plane, the control device 140 controls the scanning plane to scan the object according to the scanning parameter preset for this part, and to obtain scan data.

In some embodiments, when the second scanning stage scans a part of the object, the control device adjusts the scanning parameter of the second scanning stage based on an analysis result of the processing device corresponding to the part, to cause the second scanning stage to output the second digital signal As such, when the part of the object 120 has passed through all the scanning planes, the system integrates all the scan data, and reconstructs the object using a single-energy or spectral CT reconstruction algorithm to obtain a final 3D CT reconstruction result as well as identifies contraband and generates alarms.

Figure 3A:
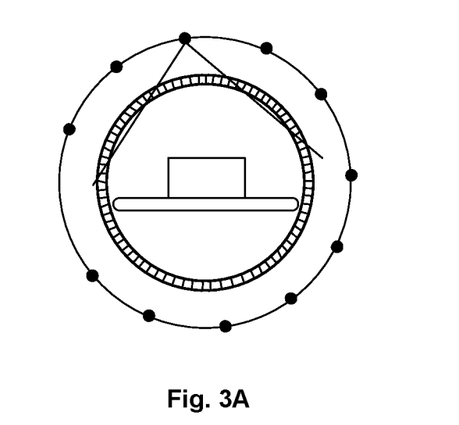
FIGS. 3A, 3B, and 3C are schematic diagrams illustrating a sparse-view scanning mode used in respective scanning stages of a CT system according to an embodiment of the disclosure.
Figure 3B:
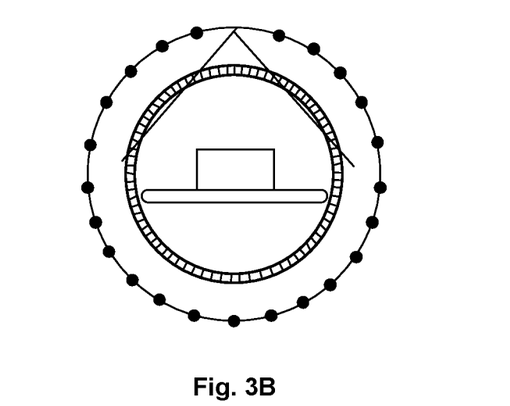
Figure 3C:
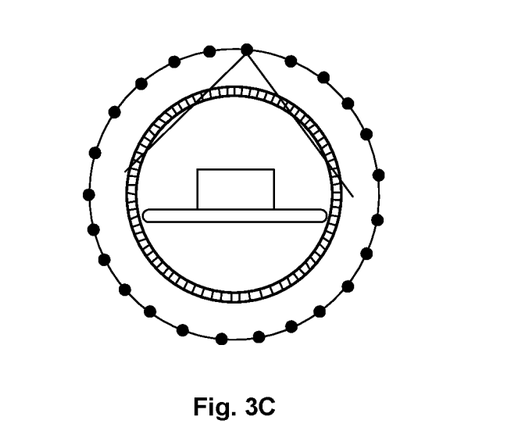
Figure 4A:
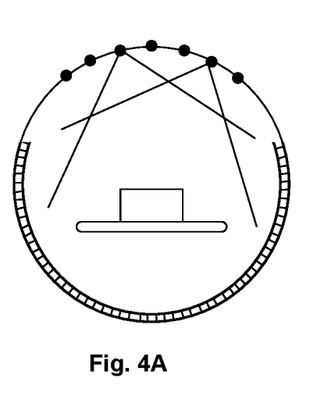
FIGS. 4A, 4B, and 4C are schematic diagrams illustrating a limited-angle scanning mode used in respective scanning stages of a CT system according to an embodiment of the disclosure.
Figure 4B:
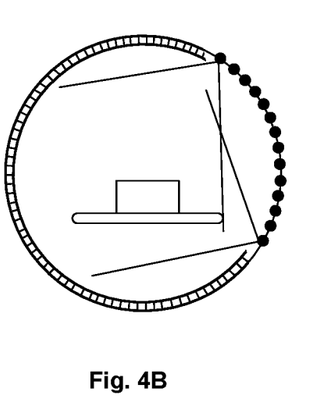
Figure 4C:
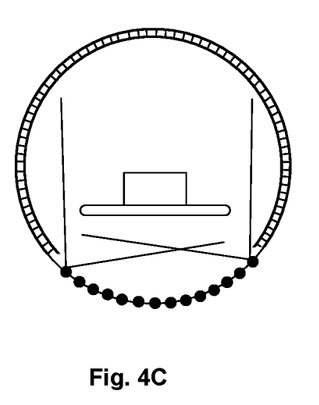

In some embodiments, the distributed ray sources and the detectors are distributed on three circular rings spaced from each other. The planes A, B and C are the first, second and third scanning planes respectively, as shown in FIG. 1. The sources in each plane may be sparsely arranged as shown in FIGS. 3A, 3B and 3C, or densely arranged within a limited angle range as shown in FIGS. 4A, 4B and 4C.

In the above embodiments, a multi-source X-ray emission device is used to irradiate luggage from different angles, and thus a rotation device in the normal CT system can be omitted, thereby reducing system cost and increasing detection accuracy. The multi-plane scanning mode further improves scanning speed. Use of distributed ray sources provides flexibility. By adjusting the energy for ray sources based on pre-processing results and incorporating multi-spectrum ray detection technology, it is possible to improve identification of dangerous and suspicious objects, such as flammable material, explosives and drugs, and to accommodate requirements of security inspection in various scenarios.

The embodiments take full advantage of distributed ray sources, and develop a new control method. Distributing the ray sources over multiple scanning planes makes it possible to adjust spectrum, beam intensity and number of the ray sources according to the object's characteristics. When the object passes through the first plane, a pre-reconstruction result can be obtained using a sparse-view or limited-angle reconstruct method, and then the spectrum, beam intensity and number for the subsequent two planes can be changed based on the analysis result and requirements. In this way, an optimal reconstruction result can be obtained on one hand, and reconstruction results at different energy levels can also be obtain on the other hand to realize material identification.

In some embodiments, the problem of data synchronization between different planes needs to addressed when the ray sources and detectors are distributed over multiple locations. By triggering the X-ray sources to emit beams in a tape-coding method, it is possible to ensure that detectors in different planes acquire data of the same plane of the object. Alternatively, time differences between time points when the object passes through several planes of detectors may be determined according to the fixed locations of the several planes, and thus corresponding data may be extracted.

In some embodiments where data at different energy levels and different angles are to be combined for reconstruction, data at all the angles may be first reconstructed using the normal single-energy CT reconstruction algorithm. The reconstruction result maintains an accurate geometric structure. Then, by using the geometric structure as a priori knowledge, scan data may be grouped and reconstructed on a group basis according to the beam energy of the source points, to obtain a reconstruction result of different X-ray energy levels.

The foregoing detailed description has set forth various embodiments of CT system and method by use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the esprit or essence of the disclosure. It should be understood that the embodiments are not limited to any of the foregoing details, and shall be interpreted broadly within the esprit and scope as defined by the following claims. Therefore, modifications and alternatives falling within the scope of the claims and equivalents thereof are to be encompassed by the scope of the present disclosure which is defined by the claims as attached.

What is claimed is:

1. A Computed Tomography (CT) system, comprising:
    a conveyor mechanism configured to convey and move an object under inspection linearly;
    a first scanning stage comprising a first ray source, a first detector, and a first data acquisition device, and configured to scan the object and generate a first digital signal;
    a second scanning stage configured to be spaced from the first scanning stage at a preset distance in a direction of the object's movement, and comprising a second ray source, a second detector, and a second data acquisition device;
    a third scanning stage comprising a third ray source, a third detector, and a third data acquisition device;
    a processing device configured to reconstruct a CT image of the object at a first image quality based on the first digital signal, and analyze the CT image; and
    a control device configured to adjust a scanning parameter of the second scanning stage based on an analysis result of the processing device to cause the second scanning stage to output a second digital signal,
    wherein the processing device is further configured to reconstruct a CT image of the object at a second image quality higher than the first image quality at least based on the first digital signal and the second digital signal;
    wherein the control device is further configured to adjust a scanning parameter of the third scanning stage based on the CT image of at least the first image quality to cause the third scanning stage to output a third digital signal, and
    wherein the processing device is further configured to reconstruct a CT image of the object at a third image quality higher than the first image quality at least based on the first digital signal, the second digital signal, and the third digital signal.

2. The CT system according to claim 1, wherein when the second scanning stage scans a part of the object, the control device adjusts the scanning parameter of the second scanning stage based on an analysis result of the processing device corresponding to the part, to cause the second scanning stage to output the second digital signal.

3. The CT system according to claim 1, wherein when the third scanning stage scans a part of the object, the control device adjusts the scanning parameter of the third scanning stage based on an analysis result of the processing device corresponding to the part, to cause the third scanning stage to output the third digital signal.

4. The CT system according to claim 1, wherein each of the first, second and third scanning stages uses a sparse-view scanning mode.

5. The CT system according to claim 1, wherein each of the first, second and third scanning stages uses a limited-angle scanning mode.

6. The CT system according to claim 1, wherein each of the first, second and third ray source comprises a plurality of source points provided in a plurality of scanning planes perpendicular or nearly perpendicular to the direction of the object's movement, and in each of the scanning planes the source points are distributed along one or more continuous or discontinuous segments of line or arc.

7. The CT system according to claim 6, wherein the source points of the second scanning stage are preset to use an increased voltage to increase ray energy when the analysis result of the processing device indicates that an increased penetrability is required to discern a metal object and its neighborhood.

8. The CT system according to claim 6, wherein the source points of the second scanning stage are preset to use an increased number of ray sources to increase a spatial resolution when the analysis result of the processing device indicates that it is required to discern tiny objects.

9. The CT system according to claim 6, wherein the source points of the second scanning stage are adjusted to have a preset number of activated ray sources when the analysis result of the processing device indicates that it is required to complete scanning within a prescribed time period.

10. The CT system according to claim 6, wherein a beam spectrum for the source points of the second scanning stage is adjusted when the analysis result of the processing device indicates that a more accurate material identification is required.

11. The CT system according to claim 6, wherein a beam intensity of the source points of each of the first, second and third scanning stages is adjusted according to a number of ray sources preset in the plane where the source points are provided.

12. The CT system according to claim 11, wherein when the number of the source points is large, the beam intensity is increased to reduce beam-emitting time of each source point and thus ensure completion of scanning within a prescribed time period;
    when the number of the source points is small, a high beam intensity is used to increase a signal-to-noise ratio of scan data.

13. A method for a Computed Tomography (CT) system comprising a first scanning stage, and a second scanning stage spaced from the first scanning stage at a preset distance in a moving direction of an object under inspection and a third scanning stage,
    the method comprises:
    scanning the object by the first scanning stage during the movement of the object, and generating a first digital signal;
    reconstructing a CT image of the object at a first image quality based on the first digital signal, and analyzing the CT image;
    adjusting a scanning parameter of the second scanning stage based on an analysis result to cause the second scanning stage to output a second digital signal;

adjusting a scanning parameter of the third scanning stage based on the CT image of at least the first image quality to cause the third scanning stage to output a third digital signal;

reconstructing a CT image of the object at a second image quality higher than the first image quality at least based on the first digital signal and the second digital signal; and reconstructing a CT image of the object at a third image quality higher than the first image quality at least based on the first digital signal, the second digital signal, and the third digital signal.

14. The method according to claim 13, wherein when the second scanning stage scans a part of the object, the scanning parameter of the second scanning stage is adjusted based on an analysis result corresponding to the part, to cause the second scanning stage to output the second digital signal.

* * * * *